(12) United States Patent
Lev et al.

(10) Patent No.: US 9,141,762 B2
(45) Date of Patent: Sep. 22, 2015

(54) SYSTEM AND METHOD FOR ANALYZING AND CONTROLLING EPIDEMICS

(76) Inventors: Michal Lev, Reut (IL); Hayim Shaul, Kfar Saba (IL); Ron Lev, Reut (IL); Ran Balicer, Ramat Gan (IL)

(*) Notice: Subject to any disclaimer, the term of this patent is extended or adjusted under 35 U.S.C. 154(b) by 316 days.

(21) Appl. No.: 13/993,186

(22) PCT Filed: Dec. 13, 2011

(86) PCT No.: PCT/IL2011/000936
§ 371 (c)(1),
(2), (4) Date: Jun. 11, 2013

(87) PCT Pub. No.: WO2012/081006
PCT Pub. Date: Jun. 21, 2012

(65) Prior Publication Data
US 2013/0275160 A1    Oct. 17, 2013

Related U.S. Application Data

(60) Provisional application No. 61/423,135, filed on Dec. 15, 2010, provisional application No. 61/575,033, filed on Aug. 15, 2011.

(51) Int. Cl.
*H04M 3/42*    (2006.01)
*H04W 4/02*    (2009.01)
*G06F 19/00*   (2011.01)
(Continued)

(52) U.S. Cl.
CPC ........ *G06F 19/3431* (2013.01); *G06F 19/3493* (2013.01); *G06Q 10/04* (2013.01); *G06Q 50/24* (2013.01); *H04M 3/42357* (2013.01);
(Continued)

(58) Field of Classification Search
CPC . G06F 19/3431; G06F 19/3493; G06Q 10/04; G06Q 50/24; H04M 3/42357; H04M 3/22; H04M 2203/2094; H04W 4/023
USPC ............. 455/456.1–457, 412.2, 404.1–404.2, 455/414.1–414.4
See application file for complete search history.

(56) References Cited

U.S. PATENT DOCUMENTS 6,608,559 B1 *  8/2003  Lemelson et al. ....... 340/539.13
7,224,957 B2 *  5/2007  Spector ...................... 455/404.2
(Continued)

OTHER PUBLICATIONS

International Search Report and Written Opinion issued in PCT/IL11/00936, dated May 16, 2012.

*Primary Examiner* — George Eng
*Assistant Examiner* — Marcus Hammonds
(74) *Attorney, Agent, or Firm* — Patrick J. Hagan; Dann, Dorfman, Herrell And Skillman, P.C.

(57) ABSTRACT

A method for analyzing and controlling epidemics in which an initiating signal is received indicative of a list of newly classified carriers of an infectious disease from an authorized health authority. Location data is received for a mobile device and a mobility pattern derived from the received location data is compared with a mobility pattern of first users to determine occurrence of a proximity event, during which one of the first users was spaced from a given carrier less than a predetermined distance. The proximity event is ranked in terms of the likelihood that the given carrier was involved in the transmission of the disease during the proximity event. If the ranking of the proximity event is higher than a predetermined level, the process is repeated for the first user participating in the proximity event and for second users. Corrective action information is then transmitted.

25 Claims, 5 Drawing Sheets

(51) Int. Cl.
*G06Q 10/04* (2012.01)
*G06Q 50/24* (2012.01)
*H04M 3/22* (2006.01)

(52) U.S. Cl.
CPC ......... *H04M3/22* (2013.01); *H04M 2203/2094* (2013.01); *H04W 4/023* (2013.01)

(56) References Cited

U.S. PATENT DOCUMENTS

| | | | |
|---|---|---|---|
| 2003/0204130 A1* | 10/2003 | Colston et al. | 600/300 |
| 2006/0036619 A1* | 2/2006 | Fuerst et al. | 707/100 |
| 2006/0155580 A1 | 7/2006 | Kawamura | |
| 2006/0288253 A1 | 12/2006 | Kawamura et al. | |
| 2007/0229290 A1* | 10/2007 | Kahn et al. | 340/573.4 |
| 2008/0103368 A1 | 5/2008 | Craine et al. | |
| 2008/0130957 A1* | 6/2008 | Small | 382/115 |
| 2009/0311986 A1* | 12/2009 | Bose et al. | 455/404.1 |
| 2010/0179835 A1* | 7/2010 | Wager | 705/3 |
| 2010/0238023 A1 | 9/2010 | Kahn et al. | |
| 2010/0316196 A1* | 12/2010 | Jokinen | 379/38 |
| 2012/0112883 A1* | 5/2012 | Wallace et al. | 340/10.1 |
| 2012/0244886 A1* | 9/2012 | Blom et al. | 455/456.3 |

* cited by examiner

SYSTEM AND METHOD FOR ANALYZING AND CONTROLLING EPIDEMICS

CROSS-REFERENCE TO RELATED APPLICATIONS

This application is the U.S. National Stage of International Application No. PCT/IL2011/000936, filed Dec. 13, 2011, which claims the benefit of U.S. Provisional Application No. 61/423,135, filed Dec. 15, 2010 and U.S. Provisional Application No. 61/575,033, filed Aug. 15, 2011. The entire disclosures of each of the aforesaid applications are incorporated by reference in the present application.

FIELD OF THE INVENTION

The present invention relates to the field of data communication. More particularly, the invention relates to a system and method for analyzing and controlling epidemics using data and communication patterns.

BACKGROUND OF THE INVENTION

Analyzing and controlling epidemics is a very important issue when governmental agencies and health authorities wish to contend with their distribution. The existing methods for analyzing and simulating tracks of epidemics and infectious diseases are based on statistical and stochastic models, and the epidemiological analysis is generally made using a standalone computer with inputs obtained mainly from official health organizations. The output of existing methods is used to propose estimations regarding geographical areas that are subject to an infectious threat. However, the accuracy of such methods is low, since the existing models are not utilized in real-time, are not based on personal data and cannot be used as an effective operational system, and since they cannot assess the mobility and interaction patterns of a person that is carrying the infectious disease. As a result, health authorities are not able to receive an accurate real time assessment of the distribution of the infectious disease, which is essential to rapidly take the right decisions and efficient operations to contend with an epidemic. In addition, receiving inaccurate epidemiological data leads to an unnecessary waste of vaccines due to the inoculation of people that are not in a risk of infection, as well as inefficient utilization of health professionals' time, which may be crucial during periods of an epidemic.

All the methods described above have not yet provided satisfactory solutions to the problem of analyzing and controlling epidemics using real-time and personal data.

It is therefore an object of the present invention to provide a system and method for receiving accurate and real-time epidemiological data that can be used to control the spread of an epidemic.

It is another object of the present invention to provide accurate geographical and personal information that allows the health authorities to directly contact suspect carriers.

It is another object of the present invention to provide a method and system for allowing health authorities to make right decisions and to conduct efficient operations while controlling an epidemic.

Other objects and advantages of the invention will become apparent as the description proceeds.

SUMMARY OF THE INVENTION

The present invention provides a method for analyzing and controlling epidemics, comprising the steps of receiving an initiating signal which is indicative of a list of newly classified carriers of an infectious disease from an authorized health authority; receiving location data for a mobile device of each of said carriers; for each of said carriers, comparing a mobility pattern derived from said received location data with a mobility pattern of one or more first users to determine occurrence of a proximity event during which one of said one or more first users was spaced from a given carrier less than a predetermined distance; ranking said proximity event in terms of the likelihood that said given carrier was involved in the transmission of said disease during said proximity event; if the ranking of said proximity event is higher than a predetermined level, repeating the mobility pattern comparing and the proximity event ranking steps for the first user participating in said proximity event and one or more second users; and transmitting corrective action information in order to control spreading of said infectious disease or transmitting forensic analysis information, in response to the number and identity of users participating in each of said proximity events which have a ranking higher than said predetermined level.

In one aspect, the location data is extracted from consumer proprietary network information which is collected by data network service providers during transmission of a communication link.

In one aspect, the location data is generated by a location identifying component provided with the mobile device, for example a subscriber identity module (SIM) application, a component interfaceable with a Global Positioning System (GPS), and a component interfaceable with one or more sniffers that are spatially disposed in the vicinity of a selected geographic region.

In one aspect, the proximity event is ranked higher than the predetermined level when a pre-encounter event that also involved the user and the given carrier preceded the proximity event.

In one aspect, the pre-encounter event is the transmission of a communication link between the user and the given carrier within a predetermined time prior to the proximity event.

In one aspect, the pre-encounter event is ingress of the user and the given carrier into a common vehicle.

In one aspect, the ingress of the user and the given carrier into the common vehicle is determined by determining that the location of the user and the given carrier simultaneously changes in substantially the same direction and at substantially the same rate.

In one aspect, the method further comprises the step of determining the number of users located within the vehicle, said number being indicative of a vehicle type and of the proximity event ranking.

In one aspect, the proximity event is ranked higher than the predetermined level when the proximity event continues for more than a predetermined duration.

In one aspect, the proximity event is ranked higher than the predetermined level when an average proximity between passengers within the vehicle is less than a predetermined value.

In one aspect, the data network is a cellular network and the consumer proprietary network information is a call detail record.

In one aspect, the data network is a WiFi network or a WiMAX network.

In one aspect, the initiating signal is also indicative of policy rules or of disease information, type and/or characteristics.

In one aspect, the corrective action signal is indicative of infected locations and infected people.

In one aspect, the method further comprises the steps of classifying the user as a potential carrier if the ranking of said proximity event is higher than a predetermined level; and determining an extent of an epidemic distribution in response to a known number of carriers and potential carriers and in response to epidemic source information.

The present invention is also directed to a system for determining interpersonal interaction patterns during a period of distress, comprising a plurality of mobile communication devices each of which accessed by a different user and having a unique hardware identifier; a component for generating location data for each of said plurality of mobile devices; and a processing device for receiving said location data associated with the mobile device of selected users known to require assistance during a period of distress and for generating from said received location data a mobility pattern for each of said selected users, wherein said processing device is operable to determine occurrence of a proximity event, by means of said mobility pattern, between each of said selected users and a corresponding additional user, to rank said proximity event in terms of the likelihood that, during said proximity event, said corresponding additional user was also made to be in need of said assistance, to classify said corresponding additional user as a potential beneficiary of said assistance when said proximity event was ranked higher than a predetermined level, and to transmit a corrective action signal to an authority to indicate the nature or scope of assistance that is required for the selected users and the classified potential beneficiaries.

In one embodiment, the selected user is a carrier of an infectious disease, the assistance is receiving a vaccine for said disease, and the potential beneficiary is a potential carrier of said disease.

In one aspect, the system further comprises a health authority server for transmitting an initiating signal which is indicative of a list of newly classified carriers of said disease to the processing device.

In one aspect, the health authority server is operable to receive a defining signal from an authorized health entity to indicate that someone has been diagnosed as being a carrier of the infectious disease.

In one aspect, the defining signal is indicative of carrier identifying information including name, address, identification number and hardware identifier.

In one aspect, the processing device comprises an evaluation module for determining a ranking of a proximity event and a potential carrier database in which is stored identifying information of all classified potential carriers.

In one aspect, the evaluation module is operable to assign a ranking higher than the predetermined level upon determining that a pre-encounter event that also involved the user and the carrier preceded the proximity event.

In one aspect, the location generating component is stored in each of the plurality of mobile devices.

In one aspect, the location generating component is stored in a data network service provider center and is operable to provide consumer proprietary network information associated with each of the plurality of mobile devices which is collected during transmission of a communication link therewith.

In one aspect, the processing device comprises a user mobility log generator for extracting location data from the consumer proprietary network information and for generating the mobility pattern thereby.

In one aspect, the corrective action signal is indicative of information selected from the group consisting of real-time or near to real-time epidemic status information, epidemic distribution information, epidemic source information, risk information, strategy decisions, graphic probability maps, post processing information, and identity of the first carrier of the disease.

In one aspect, the initiating signal is indicative of information selected from the group consisting of characteristics of the disease, known ways of transmitting the disease, probability of disease transmission after being within an infectable range, time of disease incubation after having been transmitted to another person, health authority policy rules regarding what type of vaccination is required and quarantine rules, carrier identification, and information regarding known infected locations.

In one embodiment, the selected user is a trapped person, the assistance is being rescued from a fallen building site, and the potential beneficiary is a potentially trapped person.

DETAILED DESCRIPTION OF PREFERRED EMBODIMENTS

The present invention is a system and method for analyzing and controlling epidemics by acquiring data associated with interpersonal interaction patterns of a person that is carrying an infectious disease. The system combines the two different disciplines of mobile communication analysis and infectious disease control to provide health authorities with a tool that allows them to analyze epidemiological data, to get a real-time epidemic status, to make decisions, and to execute accurate preventive measures against the spread of the disease while reducing the amount of wasted vaccines.

Since a high percentage of the world population holds or accesses a mobile device on a regular basis during the course of a day, the location of the mobile device is also indicative of the location of one who is using the mobile device. Every mobile device has a hardware identifier, e.g. a Media Access Control (MAC) address, by which it is identified within the data network providing the communication link. The hardware identifier is therefore associated with the mobile device user, allowing the whereabouts of each user to be traced. A user mobility log (UML) stores data as to where and when a specific user was located, who was near the user and for how long. By analyzing this data it is possible to define the interpersonal interaction patterns of the user. Thus an interpersonal interaction pattern processor (IIPP) is able to inform health authorities which people were within an infectable range of a person who is known to carry an infectious disease (hereinafter the "carrier"). The acquisition of this real-time epidemiological data will help health authorities to monitor the spreading of the infectious disease and to suggest actions to take for limiting the scope of a potential or actual epidemic.

Only upon an outbreak of an infectious disease that potentially can be an epidemic is operation of the UML and IIPP lawfully permitted. The data on which the UML is based is considered to be consumer proprietary network information (CPNI), i.e. data collected by data network service providers associated with a communication link, including the type of data network with which the mobile device interfaced, the hardware identifier, the location of the mobile device during the communication link, and the time, date, duration and destination identifier of the communication link. Non-limitative examples of a data network in conjunction with which the UML data is acquired include a cellular network, a WiFi network and a WiMAX network.

When the data network is a cellular network, for example, the CPNI may be extracted from a Call Detail Records (CDR), which is a computerized record that logs the number of the calling party, the number of the called party, when the call started, the duration of the call, the phone number charged for the call, an indication of whether the call was answered, the route by which the call entered the exchange, the route by which the call left the exchange, the call (or communication link) type, such as a real-time voice transmitted call or an SMS, and the location of the mobile device during the call. A cellular network service provider generates millions of CDRs per day to maintain a sufficient amount of information concerning the network customers in order to permit compilation of the UML.

It will be appreciated that the mobile device of a user found to be within an infectable range of the carrier may be operable over the same data network, or over a different data network, as the mobile device of the carrier.

Figure 1:
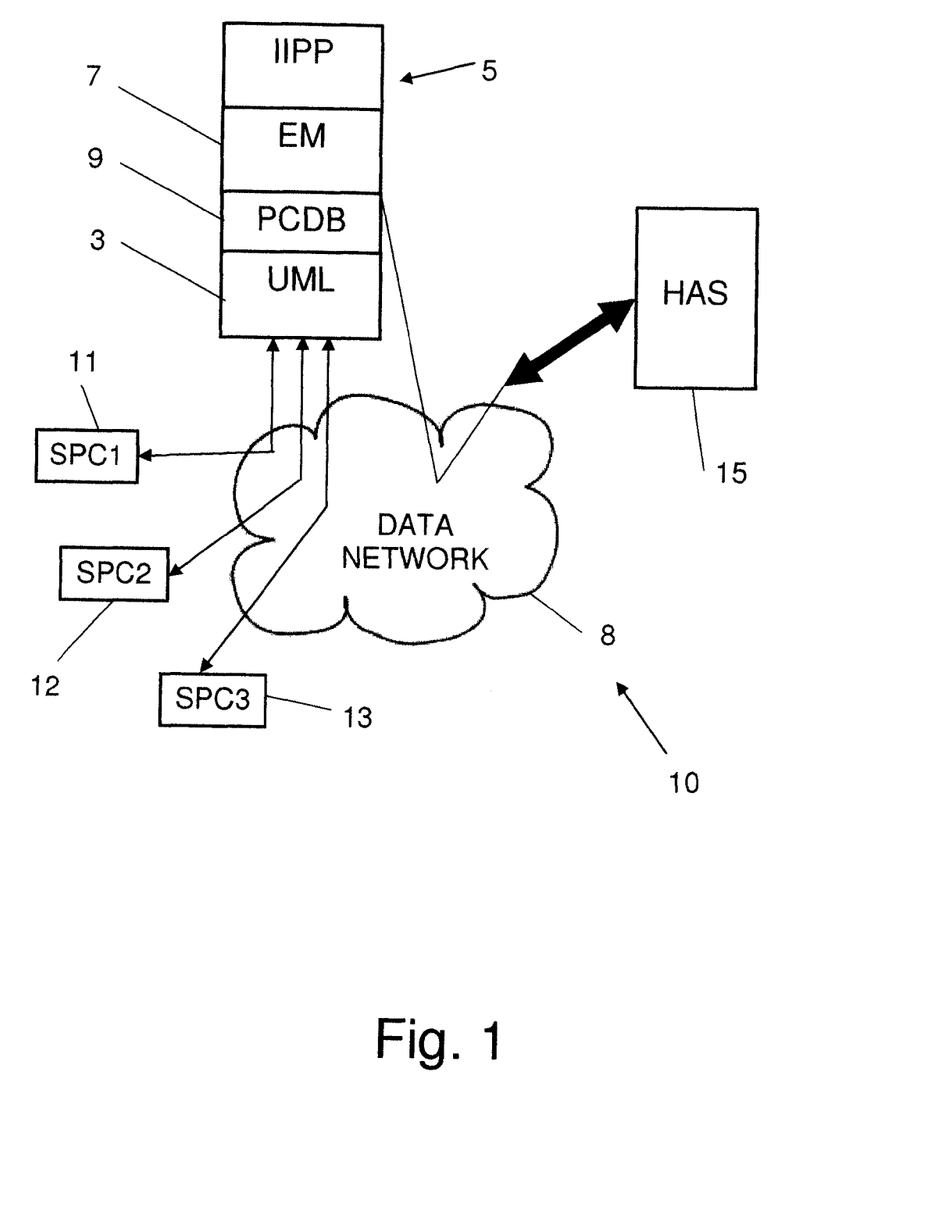
FIG. 1 is a schematic illustration of a system for analyzing and controlling epidemics, according to one embodiment of the present invention.

FIG. 1 illustrates a system generally indicated by numeral 10 for analyzing and controlling epidemics, according to one embodiment of the invention. System 10 comprises IIPP 5, which is a server that is able to generate and process an UML 3 related to each of a plurality of users. A health authority server (HAS) 15 is in data communication via network 8 with IIPP 5, and transmits thereto, when available, a list of known carriers.

IIPP 5 has a working agreement with a plurality of service providers whereby during periods of an epidemic, or when an infectious disease has been identified and has been transmitted to a plurality of carriers to such a degree so as to be classified as a potential epidemic, it can lawfully receive via network 8 the CPNIs of specified carriers or potential carriers. IIPP 5 is adapted to generate an UML for each of the carriers and to determine, based on the generated log, which users were found to be within a predetermined proximity of each of the carriers. IIPP 5 comprises an evaluation module (EM) 7 suitably programmed for determining which of those users are considered "potential carriers", as will be described hereinafter. Each service provider has a center equipped with a server, i.e. a service provider center (SPC), from which CPNIs are transmittable to IIPP 5. Three SPCs 11-13 are illustrated, each of which located in a different geographical region or operable for monitoring transmission of communication links in a different data network; however, it will be appreciated that any other number of SPCs may be in data communication with IIPP 5.

IIPP 5 is able to process data associated with the UMLs for the purpose of carrier encounter evaluation. An "encounter", as referred to herein, occurs when a first user is spaced less an infectable range from a second user for a predetermined period of time. Thus when the second user is a carrier, the first user is rendered a potential carrier due to the high probability that the infectious disease has been transmitted to the first user. The accuracy of the carrier encounter prediction depends on the resolution and accuracy of the UML database.

IIPP 5 may also comprise a potential carrier database (PCDB) 9 in which is stored a mobile device hardware identifier of each potential carrier classified by EM 7. An UML may be generated for each potential carrier, in order to determine with whom the potential carrier had an encounter. If the potential carrier was found by means of the UML to have stayed home for a long time period, an alert signal may be transmitted from IIPP 5 to HAS 15, to determine whether the potential carrier has been infected by the disease. Thus IIPP 5 is able to predict an epidemic distribution trend, determining to which geographical region the epidemic is liable to spread and transmitting information regarding this prediction by a suitable signal to HAS 15. By predicting an epidemic distribution trend, system 10 provides an efficient way for analyzing and controlling an epidemic or any infectious disease in real time or in near to real-time, in order to reduce the amount of vaccines that is needed. Alternatively, health authorities may authorize the development of a proper vaccine or to immunize the public in a few phases based on the output of IIPP 5.

Figure 2:
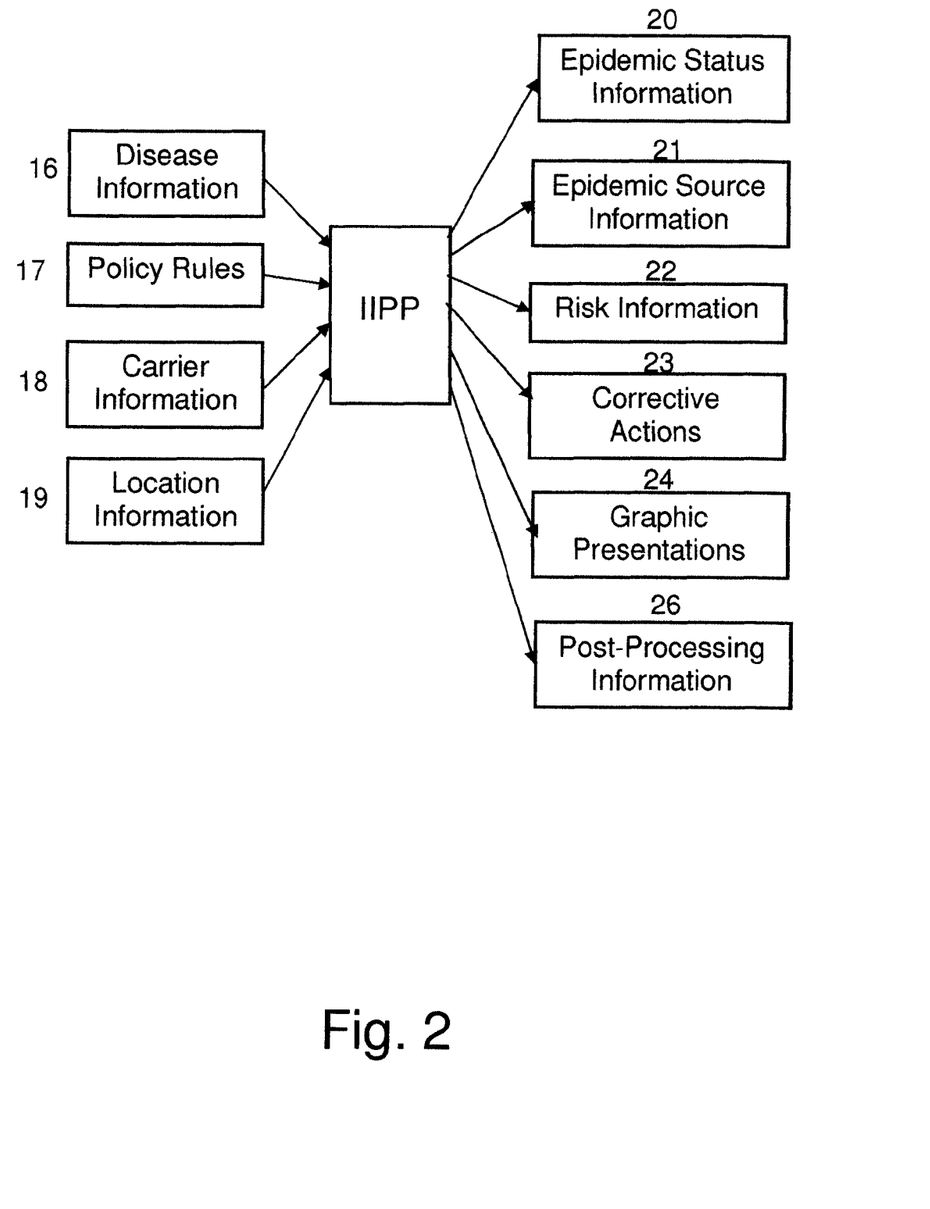
FIG. 2 is a schematic illustration of the various inputs and outputs that are achievable with use of an interpersonal interaction pattern processor.

FIG. 2 illustrates various inputs to, and outputs from, IIPP 5 that are made possible by the system of the invention.

The inputs may include disease information 16, such as characteristics of the disease, known ways of transmitting the disease, probability of disease transmission after being within the infectable range, and time of disease incubation after having been transmitted to another person, and current health authority policy rules 17, such as what type of vaccination is required and whether all carriers or all people located in a certain geographical region having more than a predetermined percentage of carriers have to be quarantined. Other inputs are carrier information 18 including carrier identification and information regarding infected locations, location information 19 received from one or more SPCs or directly from a mobile device.

The outputs of IIPP 5 may include epidemic status information 20 as to what extent the epidemic has spread, if at all, epidemic source information 21 regarding locations having an above average percentage of the local population that are infected by the disease or an above average number of people that are infected by the disease, risk information 22 providing a prioritized list of those that are in risk of being infected including hardware identifiers, corrective actions 23 to be taken such as strategy decisions, graphic presentations 24 such as graphic probability maps for past and future scenarios, and post processing information 26 regarding an analysis of how health authorities handled the epidemic. While generating post processing information 26, IIPP 5 may be operable to determine the identity of "patient zero", or the first carrier of the infectious disease. Knowledge regarding the epidemic distribution following this index case will be useful in assessing performance of health authorities.

Figure 3:
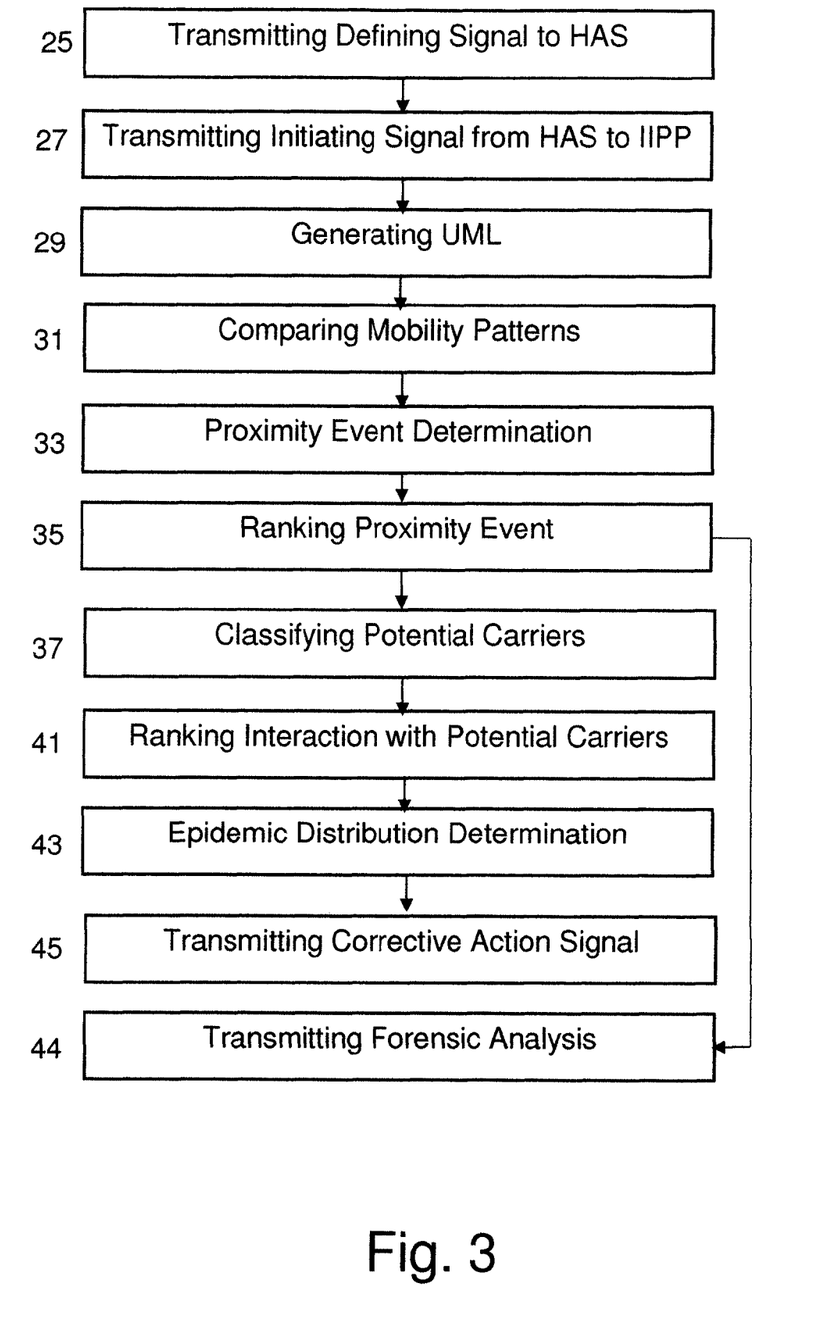
FIG. 3 is a method for analyzing and controlling epidemics, according to one embodiment of the present invention.

FIG. 3 illustrates a method for analyzing and controlling epidemics, according to one embodiment of the invention. Firstly, an authorized health entity transmits a defining signal in step 25 to the HAS to indicate that someone has been diagnosed as being carrier of a known infectious disease. Conversely, a defining signal is also transmitted to the HAS after someone has been diagnosed as no longer being a carrier of the infectious disease.

Carrier identifying information, including name, address, identification number, hardware identifier, and possibly a home phone number, is transmitted together with the defining signal. The hardware identifier may be determined by the IIPP, by an SPC, or by other means. The authorized health entity transmitting the defining signal may be a physician who personally diagnosed the disease, an official institute such as a health organization or a hospital that received documentation from a physician concerning the carrier, or an authorized call center that received during the course of a call, e.g. a voice call, SMS, USSD or WAP applications, admission that the caller is a carrier of the infectious disease.

Unstructured Supplementary Service Data (USSD) applications are used to send text information between a mobile phone and an application program in the data network. Wireless Application Protocol (WAP) is a specification for a set of communication protocols to standardize the way that wireless devices can be used for Internet access.

Alternatively, the authorized health entity may be a laboratory that analyzed a test specimen taken from a sick person and concluded, based on the laboratory results, that the sick person is a carrier. A computer may automatically transmit the defining signal after receiving the laboratory results, or a laboratorian may personally transmit the defining signal.

The HAS in turn transmits in step 27 an initiating signal which is indicative of a list of newly classified carriers or of an updated list of carriers to the IIPP. After receiving the initiating signal, the IIPP generates an UML in step 29 for each newly classified carrier by receiving CPNIs associated with the carrier hardware identifier from one or more SPCs. The UML determines the mobility pattern of the carrier during the course of a day, i.e. whether the carrier remained at the same location or had a change in location. Each location visited by the carrier, i.e. intentionally or unintentionally, for social, business or recreational purposes, and the time and duration of the visit are stored in the IIPP.

The IIPP compares the mobility pattern of the carrier with other users in step 31 in order to identify potential carriers. Since the IIPP also receives CPNIs associated with other users from the SPCs, the IIPP is able to determine the occurrence of a proximity event in step 33 during which a user was spaced from the carrier less than a predetermined proximity, e.g. 50 m. The IIPP then ranks in step 35 each proximity event by means of the evaluation module in terms of the likelihood that the proximity event is indicative of an encounter which causes the user to be infected by the disease. A proximity event will be considered of a relatively high ranking when it is indicative of a more intimate interpersonal interaction that is liable to cause transmission of the infectious disease, for example one that continues for more than a predetermined duration, e.g. 3 minutes. The IIPP therefore classifies a user as a potential carrier in step 37 when the ranking of the proximity event is higher than a predetermined level.

The IIPP is used to evaluate an epidemic status. In step 41, the IIPP ranks the interaction between each potential carrier and other users in a similar fashion as described hereinabove with respect to a carrier. A distribution of the epidemic is determined in step 43 by knowing a real-time or near to real-time location of all carriers and potential carriers during different times of the day or during different days. The IIPP may take into account an incubation period of the disease after a potential carrier was located within the proximity of a carrier. The IIPP transmits a corrective action signal in step 45, in response to the recently determined epidemic status or in response to any other acquired epidemiological data.

The corrective action signal may be transmitted to the HAS so as to indicate the epidemic sources, for the purpose of distributing vaccines to those sources and to warn outsiders not to frequent those locations. When the number of carriers decreases, a corrective action signal is transmitted to suggest reducing the number of vaccines that are needed in that location.

Likewise the corrective action signal may be indicative of a list of potential carriers, including one or more phone numbers, to whom health professionals are recommended to contact for the purpose of convincing those potential carriers to be vaccinated. The potential carriers may be contacted by using voice calls, SMS messages, USSD applications or WAP applications.

Alternatively, the corrective action signal may be transmitted from the IIPP to a carrier or potential carrier. After the HAS transmits to the IIPP a real-time defining signal specifying which potential carriers have not yet been vaccinated, the corrective action signal may be transmitted to a potential carrier who is approaching a transportation station such as a bus station or a train station, indicating that the potential carrier is liable of infecting a large number of people at the station or following ingress into the public transport vehicle. Likewise the corrective action signal may be transmitted to a carrier who is approaching a transportation station.

Figure 4:
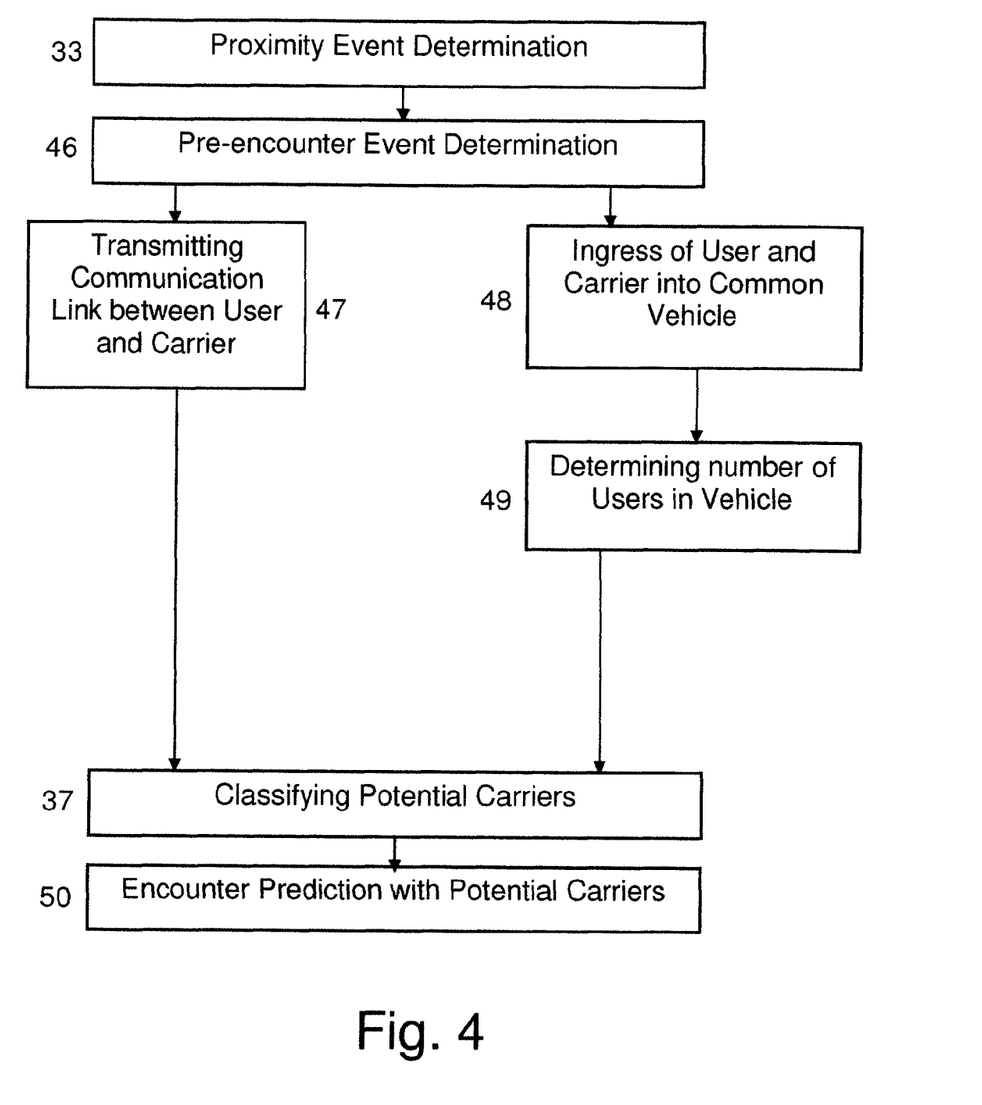
FIG. 4 is a method for performing encounter prediction.

As shown in FIG. 4, one way of determining that a proximity event is of a relatively high ranking is by performing encounter prediction. After determining the occurrence of a proximity event in step 33, the EM further processes the proximity data in step 46 by determining whether the proximity event followed a pre-encounter event common to the proximate user and the carrier. Such a proximity event therefore receives a relatively high ranking since the probability of an infection transmittable encounter between the user and the carrier is likely when a proximity event followed a pre-encounter event.

One example of a pre-encounter event is the transmission of a communication link between the user and the carrier in step 47. The occurrence of a proximity event between a user and the carrier following the transmission of a communication link therebetween is indicative that the proximity event was intentional and that there exists a high probability that the user was within an infectable range of the carrier during the proximity event.

Another example of a pre-encounter event is the ingress in step 48 of the user and carrier into a common motor vehicle, e.g. an automobile, bus and train. A trip within the motor vehicle is classified as a pre-encounter event when the IIPP determines that the location of the user and carrier simultaneously changes in the same direction and at the same rate. Thus there exists a high probability that the user was within an infectable range of the carrier when the proximity event occurred during the course of the trip. The number of users that are travelling within the vehicle is determined in step 49, the number of travelers indicating whether the vehicle is an automobile, bus or train. The proximity event will receive a higher ranking when the users are travelling together in an automobile as opposed to travelling in a train due to the smaller average proximity between passengers.

It will be appreciated that other types of pre-encounter events are also within the scope of the invention insofar as the pre-encounter event is indicative of a significant risk that an encounter with a carrier subsequently took place.

After the IIPP classifies a user as a potential carrier in step 37 due to the relatively high ranking of the proximity event as a result of the occurrence of the pre-encounter event, the EM performs prediction in step 50 of an encounter between each potential carrier and other users in a similar fashion as described hereinabove as one way to evaluate the epidemic status.

The same method may be used for post processing. Referring back to FIG. 3, the IIPP may commence post processing after receiving the initiating signal from the HAS in step 27 and the identity of carriers thereby. The IIPP generates a UML in step 29 by determining the past mobility pattern of each carrier, prior to the time when the initiating signal was received. The past mobility pattern of other users is compared with that of each carrier in step 31 in order to determine past proximity events in step 33. The IIPP then ranks the past proximity events in step 35 to determine the likelihood that the carrier was infected by a user with whom he or she interacted (hereinafter "infector"). Steps 29, 31, 33 and 35 are repeated with respect to the infector if the ranking of the proximity event was higher than a predetermined level, and likewise for an infector of the infector, for as many stages as needed until the patient zero is determined or the source of the epidemic is determined, e.g. a location accessed by all or many of the carriers. This type of post-processing method will be referred to as "forensic analysis", and the output of the forensic analysis is transmitted from the IIPP to the HAS in step 44.

Figure 5:
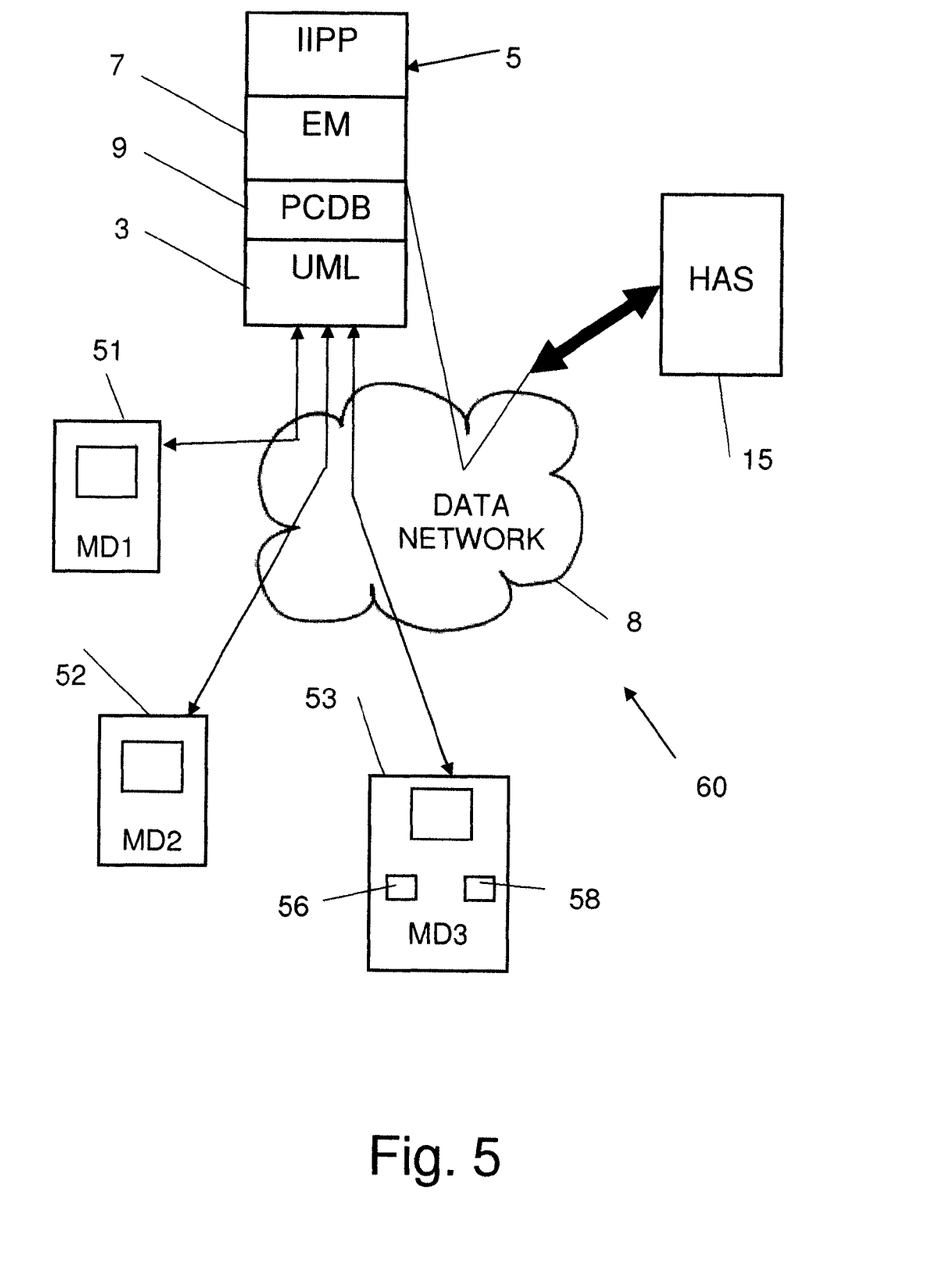
FIG. 5 is a schematic illustration of a system for analyzing and controlling epidemics, according to another embodiment of the present invention.

FIG. 5 illustrates system 60 according to another embodiment of the invention wherein location information is transmitted directly from a mobile device (MD), e.g. any of mobile devices 51-53, to IIPP 5. Mobile devices 51-53 are provided with a location identifying component 56, such as a subscriber identity module (SIM) application for receiving an instantaneous location area identifier, or a component interfaceable with a Global Positioning System (GPS) or with one or more sniffers that are spatially disposed in the vicinity of a selected geographic region, and with a dedicated application 58 for circumventing transmission of location data from a SPC to IIPP 5.

Upon receiving the initiating signal from the HAS as to the presence of carriers and that there exits a possibility that an epidemic will result, IIPP 5 transmits a command signal to a plurality of SPCs for activating the circumventing application 58 of all mobile devices with which a SPC is in communication to a circumventing mode. After circumventing application 58 is set to a circumventing mode, the location data generated by component 56 will be transmitted to IIPP 5 via data network 8. Consequently, IIPP 5 will be able to generate a UML by means of the received location data with a minimal amount of computer resources. Likewise other mobile devices will transmit their location data to IIPP 5 so that the occurrence and ranking of a proximity event can be determined.

Circumventing application 58 may be downloaded by the user to the mobile device. Application 58 may also be used by the user to receive epidemiological data from IIPP 5, such as his personal clinical situation, as well as disease, epidemic status, epidemic source and risk information.

It will be appreciated that the location data generated by component 56 is transmittable to a SPC when the mobile device is not provided with application 58.

In another embodiment, the IIPP is used for disaster management. Knowing the location of a large number of people immediately following periods of a disaster such as an earthquake is of great importance, particularly in order to prioritize the rescue efforts. Rescue forces can therefore focus their attention on locations whereat a large number of people are trapped, such as a collapsed building, rather than spending an inordinate amount of time at a site whereat only a small number of people are trapped. There is also much importance in being able to locate a specific person, especially one who is a public figure, so that the rescue forces may be directed to sites where such public figures are located.

Even though a disastrous event is usually followed by an infrastructure failure such as an electricity outage due to torn electric cables and a cellular network crash due to damaged antennas, the system can nevertheless determine the identity of many of the trapped people since the IIPP is located externally to the disaster site and is therefore assured of being operational.

After occurrence of a disastrous event, the IIPP receives an initiating signal for defining the identity of a person trapped at a specific site, including the hardware identifier of his mobile device. The initiating signal may be a voice call, a text message or any other communication link transmitted via a data network by an acquaintance of the trapped person to the IIPP. Alternatively, the IIPP generates the initiating signal by analyzing location data of various mobile devices in order to identify one located at the site of the disastrous event. The IIPP then generates an UML for each trapped person in order to determine a proximity event between the trapped person and another user, as described hereinabove. The IIPP then classifies one as being potentially trapped when the proximity event is ranked at a sufficiently high level. The IIPP is adapted to transmit a corrective action signal to a rescue force server for specifying the number of trapped and potentially trapped people that are located at a specific site. A corrective action may also be transmitted to a trapped person or to a potentially trapped person in order to provide necessary rescue information or to receive information concerning their status.

While some embodiments of the invention have been described by way of illustration, it will be apparent that the invention can be carried out with many modifications, variations and adaptations, and with the use of numerous equivalents or alternative solutions that are within the scope of persons skilled in the art, without departing from the spirit of the invention or exceeding the scope of the claims.

The invention claimed is:

1. A method for analyzing and controlling epidemics, comprising the steps of:
   a) receiving an initiating signal which is indicative of a list of newly classified carriers of an infectious disease from an authorized health authority;
   b) extracting location data and interaction data for mobile devices belonging to said newly classified carriers using Call Detail Records (CDRs) that are continuously collected and stored for all mobile device users;
   c) comparing a mobility pattern and interpersonal interaction pattern derived from said extracted location data and interaction data for each newly classified carrier of the newly classified carriers with a mobility pattern and an interpersonal interaction pattern of a plurality of mobile device users to determine encounters and occurrence of one or more proximity events, wherein during the one or more proximity events at least one first user of said plurality of mobile device users was within a predetermined distance of at least one of the newly classified carriers or social interactions occurred between said at least one first user and said at least one of the newly classified carriers;
   d) ranking said one or more proximity events in terms of the likelihood that said at least one of the newly classified carriers was involved in transmission of said infectious disease during said one or more proximity events, based on at least one of an interaction duration or a pre-encounter event;
   e) repeating steps c) and d) for the at least one first user participating in said one or more proximity events and at least one second user of the plurality of mobile device users when the ranking of said one or more proximity events is higher than a predetermined level;
   f) finding a group of users from the plurality of mobile device users that have been infected and/or having the highest probability to be infected, without being symptomatic, based on the ranking;

g) transmitting corrective action information to control spreading of said infectious disease; and h) transmitting forensic analysis information, in response to the number of mobile device users in said group of users and identification information of mobile device users participating in said one or more proximity events where said ranking is higher than said predetermined level.

2. The method according to claim 1, wherein the location and interaction data is extracted from consumer proprietary network information which is collected by data network service providers during transmission of a communication link.

3. The method according to claim 2, wherein the data network is a cellular network and the consumer proprietary network information is a call detail record of the call detail records.

4. The method according to claim 2, wherein the data network is a WiFi network or a WiMAX network.

5. The method according to claim 1, wherein the location and interaction data is generated by a location identifying component provided with the mobile device.

6. The method according to claim 5, wherein the location identifying component is a subscriber identity module (SIM) application.

7. The method according to claim 1, wherein the one or more proximity events is ranked higher than the predetermined level when the pre-encounter event involving the at least one first user and the at least one of the newly classified carriers preceded the one or more proximity events.

8. The method according to claim 7, wherein the pre-encounter event is the transmission of a communication link between the at least one first user and the at least one of the newly classified carriers within a predetermined time prior to the one or more proximity events.

9. The method according to claim 7, wherein the pre-encounter event is ingress of the at least one first user and the at least one of the newly classified carriers into a common vehicle.

10. The method according to claim 1, wherein the one or more proximity events is ranked higher than the predetermined level when the one or more proximity events continues for more than a predetermined duration.

11. The method according to claim 9, wherein the one or more proximity events is ranked higher than the predetermined level when an average proximity between the at least one first user and the at least one of the newly classified carriers within the vehicle is less than a predetermined value.

12. The method according to claim 1, wherein the initiating signal is also indicative of policy rules or of disease information, type and characteristics.

13. The method according to claim 1, wherein the corrective action signal is indicative of infected locations and infected people.

14. The method according to claim 1, further comprising the steps of:

a) classifying the at least one first user as a potential carrier when the ranking of said one or more proximity events is higher than a predetermined level; and b) determining an extent of an epidemic distribution in response to a known number of carriers and potential carriers and in response to epidemic source information.

15. A system for determining interpersonal interaction patterns during a period of distress, comprising:

a) a health authority server for transmitting an initiating signal which is indicative of a list of selected mobile device users carrying an infectious disease;

b) a plurality of mobile devices each accessed by a different mobile device user of a plurality of mobile device users and having a unique hardware identifier;

c) a component for generating location data and interaction data for each of said plurality of mobile devices, using Call Detail Records (CDRs) that are continuously collected and stored for all mobile device users; and d) a processing device for extracting said location data and interaction data associated with the mobile devices of said selected mobile device users of the plurality of mobile device known to require assistance during a period of distress and for generating from said location data and interaction data a mobility pattern and interpersonal interaction pattern for said selected mobile device users, wherein said processing device is operable to:

i. determine encounters and occurrence of one or more proximity events, by means of said mobility pattern and interpersonal interaction pattern, between at least one of said selected mobile device users and at least one corresponding additional mobile device user of the plurality of mobile device users, wherein during the one or more proximity events said at least one corresponding additional mobile device user was within a predetermined distance of said at least one of the selected mobile device users or social interactions occurred between said at least one corresponding additional mobile device user and said at least one of the selected mobile device users;

ii. rank said one or more proximity events in terms of the likelihood that, during said one or more proximity events, said at least one corresponding additional mobile device user was in need of said assistance, based on at least one of an interaction duration or a pre-encounter event;

iii) repeat steps i, and ii, for said at least one corresponding additional mobile device and at least one second corresponding mobile device user of the plurality of mobile device users when the ranking of said one or more proximity events is higher than a predetermined level;

iv. find a group of users of the plurality of mobile device users that have been infected and/or having the highest probability to be infected, without being symptomatic, based on the ranking;

v. classify said at least one corresponding additional mobile device user as one or more potential beneficiaries of said assistance when said one or more proximity events was ranked higher than said predetermined level; and vi. transmit a corrective action signal to an authority to indicate the nature or scope of assistance that is required for said selected mobile device users and the one or more potential beneficiaries;

vii. transmit forensic analysis information, in response to the number of users in said group of users and identification information of mobile device users participating in said one or more proximity events where said ranking is higher than said predetermined level.

16. The system according to claim 15, wherein the selected mobile device users is a carrier of an infectious disease, the assistance is receiving a vaccine for said disease, and the one or more potential beneficiaries are potential carriers of said disease.

17. The system according to claim 16, further comprising transmitting the initiating signal which is indicative of a list of newly classified carriers of said disease to the processing device.

18. The system according to claim 17 wherein the health authority server is operable to receive a defining signal from an authorized health entity to indicate that someone has been diagnosed as being a carrier of the infectious disease.

19. The system according to claim 16, wherein the processing device comprises an evaluation module for determining the ranking of one or more proximity events and a potential carrier database which stores identifying information of all classified potential carriers.

20. The system according to claim 19, wherein the evaluation module is operable to assign a ranking higher than the predetermined level upon determining that the pre-encounter event involving the at least one corresponding additional user and the at least one selected mobile device user preceded the one or more proximity events,
    involving the at least one first user and the at least one of the newly classified carriers preceded the one or more proximity events.

21. The system according to claim 16, wherein the initiating signal is indicative of information selected from the group consisting of characteristics of the disease, known ways of transmitting the disease, probability of disease transmission after being within an infectable range, time of disease incubation after having been transmitted to another person, health authority policy rules regarding what type of vaccination is required and quarantine rules, carrier identification, and information regarding known infected locations.

22. The system according to claim 15, wherein the location generating component is stored in each of the plurality of mobile devices.

23. The system according to claim 15, wherein the location generating component is stored in a data network service provider center and is operable to provide consumer proprietary network information associated with each of the plurality of mobile devices which is collected during transmission of a communication link therewith.

24. The system according to claim 15, wherein the corrective action signal is indicative of information selected from the group consisting of real-time or near to real-time epidemic status information, epidemic distribution information, epidemic source information, risk information, strategy decisions, graphic probability maps, post processing information, and identity of the first carrier of the disease.

25. The system according to claim 15, wherein the at least one selected mobile device user is a trapped person, the assistance is being rescued from a fallen building site, and the one or more potential beneficiaries is a potentially trapped user.

* * * * *